US006441034B1

(12) United States Patent
Roy

(10) Patent No.: US 6,441,034 B1
(45) Date of Patent: Aug. 27, 2002

(54) INSECT REPELLENT

(76) Inventor: Reynald Roy, 21 Nowlan Street, Grand Falls, New Brunswick (CA), E3Z 1B2

( * ) Notice: Subject to any disclaimer, the term of this patent is extended or adjusted under 35 U.S.C. 154(b) by 0 days.

(21) Appl. No.: 09/361,188

(22) Filed: Jul. 29, 1999

(30) Foreign Application Priority Data

Aug. 27, 1998  (CA) .............................................. 2246795

(51) Int. Cl.$^7$ ........................ A01N 37/10; A01N 37/18
(52) U.S. Cl. ...................................................... 514/544
(58) Field of Search ................................ 514/646, 506, 514/648, 544, 617; 424/405

(56) References Cited

U.S. PATENT DOCUMENTS 3,859,121 A * 1/1975 Yeadon et al. .............. 514/221
3,989,831 A * 11/1976 Lacefield .................... 424/249
5,196,200 A * 3/1993 Wilson et al. ............... 424/411
5,885,600 A * 3/1999 Blum et al. ................. 424/405

FOREIGN PATENT DOCUMENTS

| BE | 906136 | * | 4/1987 |
| FR | 2455459 | * | 1/1981 |
| SU | 1595523 | * | 9/1990 |

* cited by examiner

*Primary Examiner*—Alton Pryor
(74) *Attorney, Agent, or Firm*—George A. Seaby

(57) ABSTRACT

A crystal clear, transparent insect repellent in gel form contains N,N-diethyl-m-toluamide (DEET), water, a lower alcohol, preferably ethanol, carboxypolymethylene as a gelling agent, triethanolamine for neutralizing the gelling agent, methyl and propyl paraben, a perfume for masking the odor of the DEET, and a polysorbate, preferably polyoxyethylene (20) sorbitan monolaurate for improving the texture of the gel.

4 Claims, No Drawings

INSECT REPELLENT

BACKGROUND OF THE INVENTION

1. Field of the Invention

This invention relates to an insect repellent, and in particular to an insect repellent utilizing DEET as the active ingredient.

2. Discussion of the Prior Art

DEET is the generic name for N,N-diethyl-3-methylbenzamide or N,N-diethyl-m-toluamide. The compound has known insect repellent properties (see for example the details provided on pages 1 and 2 of Canadian Patent No. 1,196,278, which issued to E. Charlet et al on Nov. 5, 1985). A variety of another DEET formulations are described in the patent literature.

U.S. Pat. No. 2,403,389, issued to S. I. Gertler on Oct. 1, 1946 discloses DEET-containing insect repellent compositions in the form of a cream, a lotion or a dusting powder.

Canadian Patent No. 887,035, issued to B. T. Gillis on Nov. 30, 1971 discloses a liquid insect repellent which may contain DEET and a solvent selected from a variety of lower alcohols, glycols and hexachloroprene.

Canadian Patent No. 1,106,278, issued to A. Petnakaran on Feb. 4, 1982, discloses a black fly repellent consisting of DEET and vanillin.

Canadian Patent No. 1,196,278, issued to E. Charlet et al on Nov. 5, 1985 describes an insect repellent consisting essentially of DEET in an alcoholic solution and polyethylene glycol.

Canadian Pat. No. 1,196,279, issued to E. Charlet et al on Nov. 5, 1995 relates to an insect repellent containing DEET in an alcoholic solution and castor oil. The composition may also contain water.

Most commercially available, DEET-containing compositions are oily liquids or sprayable solutions. When an oily composition is applied to the skin, the result is a greasy film which dries relatively slowly. When applying a more quick drying spray, it is difficult to produce a uniform coating. In order to coat the entire surface of an area of skin, it is necessary to liberally spray the area often using a large volume of repellent.

GENERAL DESCRIPTION OF THE INVENTION

An object of the present invention is to provide an insect repellent in semi-solid gel form, which can easily be applied in a uniform manner.

Another object of the invention is to provide DEET-containing insect repellent which dries relatively quickly and does not leave a greasy deposit on the skin.

DESCRIPTION OF THE PREFERRED EMBODIMENT

The above listed object are accomplished in accordance with the present invention by an insect repellent in gel form comprising by weight 5 to 35% N,N-diethyl-m-toluamide; 40 to 60% water; 20–50% a lower alcohol; 0.2 to 1.2% gelling agent selected from the group consisting of carboxypolymethylene and a lower hydroxy cellulose; 0.0 to 1.7% polysorbate; and 0.1 to 1.0% base selected from the group consisting of alkali metal hydroxides and lower alcohol amines.

A good product, i.e. clear, transparent gel includes by weight 9–11% N,N-diethyl-m-toluamide, 50–55% water, 35–40% ethanol; 0.5–0.9% carboxypolymethylene, 0.0–1.2% polyoxyethylene sorbitan monolaurate; 0.3–0.4% triethanolamine, 0.08–0.12% of each of methyl and propyl paraben, and 0.3–0.5% perfume.

In accordance with a preferred embodiment of the invention, the repellent contains by weight 10% N,N-diethyl-m-toluamide; 50.204% water; 37.05 ethanol; 0.7% carboxypolymethylene; 1.11% polyoxyethylene (20) sorbitan monolaurate; 0.336% triethanolamine; 0.1% methyl paraben; 0.1% propyl paraben and 0.4% perfume.

In the compositions set out above, the active ingredient is DEET or N,N-diethyl-m-toluamide, which is dissolved in a lower alcohol such as ethanol, isopropanol or a mixture thereof. The preferred alcohol is ethanol, which evaporates slightly more quickly and has a more pleasant odor than isopropanol.

The repellent composition is gelled using a variety of gelling agents including carboxypolymethylene or a hydroxy cellulose such as hydroxyethyl cellulose, hydroxypropyl cellulose, hydroxypropyl methyl cellulose and carboxymethyl cellulose. However, the preferred gelling agent is carboxypolymethylene (commonly known as carbomer or carbopol). The use of carboxypolymethylene results in a clear, transparent gel. When using carboxypolymethylene as the gelling agent, a base such as an alkali metal hydroxide or a lower alcohol amine (preferably triethanolamine) is used to neutralize the gelling agent. The hydroxide or amine is also used to adjust the pH of the repellant.

A paraben such as methyl and/or propyl paraben is used as a preservative, i.e. to extend the shelf life of the repellent composition.

The polyoxylethylene (20) sorbitan monolaurate or Polysorbate 20 available under the trade name TWEEN is an emulsifier, which improves the texture of the composition. A suitable gel can be produced without the polysorbate but, because the compound improves the texture of the gel, it is normally included.

While a perfume is not absolutely necessary, the use of a perfume is preferred to mask the odor of the N,N-diethyl-m-toluamide (DEET). While the preferred perfume is Oil of Freesia, other commercially available perfumes can be used in the composition.

The first step in the preparation of the composition is to dissolve methyl paraben in water. The carboxypolymethylene (carbomer) is added to water and mixed with the methyl paraben solution. The carbomer forms a slurry, which is left standing in the water for 30 to 60 minutes to let the carbomer fibers swell in the presence of water.

Propyl paraben is dissolved in ethanol and DEET is added to the resulting solution. The alcoholic solution of propyl paraben and DEET is added to the mixture of methyl paraben, carbomer and water.

The perfume (Oil of Freesia) and the Polysorbate 20 are added to the above described DEET composition.

Finally, triethanolamine is added to the mixture, and the gel is homogenized. The pH of the gel is 6.3–6.8. As mentioned above, the gel is transparent and crystal clear. The repellent thus produced spreads easily and uniformly on the skin.

I claim:

1. An insect repellent in gel form consisting essentially of by weight. 5 to 35% N,N-diethyl-m-toluamide; 40 to 60% water; 20–50% lower alcohol; 0.2 to 1.2% gelling agent selected from the group consisting of carboxypolymethylene and a lower hydroxy cellulose; 0.0 to 1.7% polysorbate; 0.1 to 1.0% base selected from the group consisting of alkali metal hydroxides and lower alcohol amines; and 0.15% paraben.

2. An insect repellent according to claim 1, wherein the paraben is selected from the group consisting of methyl paraben and propyl paraben.

3. An insect repellent in gel form consisting essentially of by weight, 5 to 20% N,N-diethyl-m-toluamide; 50 to 55% water; 35 to 40% ethanol; 0.5 to 0.9% carboxypolymethylene; 0.0 to 1.2% polyoxyethylene (20) sorbitan monolaurate; 0.3 to 0.4% triethanolamine; 0.08 to 0.12% methyl paraben; 0.08 to 0.12% propyl paraben; and 0.3 to 0.5% perfume.

4. An insect repellent in gel form consisting essentially of in percentages by weight 10% N,N-diethyl-m-toluamide; 50.204% water; 37.05% ethanol; 0.7% carboxypolymethylene; 1.11% polyoxyethylene (20) sorbitan monolaurate; 0.336% triethanolamine; 0.1% methyl paraben; 0.1% propyl paraben and 0.4% oil of freesia.

* * * * *